United States Patent [19]

Tomioka et al.

[11] 4,235,633

[45] Nov. 25, 1980

[54] DENTAL COMPOSITIONS

[75] Inventors: Kentaro Tomioka, Chofu; Shunichi Futami, Nagareyama, both of Japan

[73] Assignee: G-C Dental Industrial Corporation, Tokyo, Japan

[21] Appl. No.: 3,792

[22] Filed: Jan. 16, 1979

[30] Foreign Application Priority Data

Jan. 27, 1978 [JP] Japan ................................. 53-7380

[51] Int. Cl.³ .......................... C08L 93/04; C09K 3/00
[52] U.S. Cl. ...................................... 106/35; 106/177; 106/219; 260/30.6 R; 260/998.11
[58] Field of Search ........................... 106/35, 177, 35; 260/963, 987, 448 R, 30.6 R, 998.11, 30.6

[56] References Cited

U.S. PATENT DOCUMENTS

| | | | |
|---|---|---|---|
| 2,329,707 | 9/1943 | Farrington et al. | 260/963 |
| 3,028,247 | 4/1962 | Molnar | 106/35 |
| 3,837,865 | 9/1974 | Pellico | 106/35 |
| 4,036,950 | 7/1977 | Baines et al. | 424/57 |
| 4,039,636 | 8/1977 | Claus et al. | 260/987 |
| 4,152,421 | 5/1979 | Tsutsumi et al. | 260/963 |

FOREIGN PATENT DOCUMENTS 605983 11/1936 Fed. Rep. of Germany ............. 106/35

*Primary Examiner*—Theodore Morris
*Attorney, Agent, or Firm*—Oblon, Fisher, Spivak, McClelland and Maier

[57] ABSTRACT

A novel dental composition is provided, which comprises; a combination of 8 to 92% by weight of liquid acid phosphates obtained by replacing one or two hydrogen atoms of orthophosphoric acid with alcohols having 3 to 13 carbon atoms and being essentially insoluble in water, and 92 to 8% by weight of at least one of reactive multivalent metallic salts selected from the group consisting of oxides, hydroxides, basic salts and silicates of alkaline earth metals, aluminium or heavy metals, said compounds being permitted to react with each other such that they are cured at room temperature. This composition may further contain liquid organic carboxylic acid having 6 or more carbon atoms, solid organic carboxylic acid having 5 or less carbon atoms and fluorine compounds in the form of fluorides silico fluorides titanium fluorides, and zirconium fluorides.

6 Claims, No Drawings

DENTAL COMPOSITIONS

BACKGROUND OF THE INVENTION

The present invention relates to a moldable dental composition which can firmly be bound and cured in a short time interval at room temperature. The present invention provides dental compositions which are especially useful as filling materials for the pulp canal, temporal filling materials for broken teeth, temporal cements for metal inlays or crowns, impression materials for obtaining a negative of the hard and soft tissues of the oral cavity, fixing materials for correcting the irregularities of the teeth, restorative materials for dentures or materials for other therapeutic uses.

Heretofore, for such purposes, use has long been made of a zinc oxide/eugenol based material composed mainly of eugenol or clove oil, resin and zinc oxide, which is separated into two component phases, liquid and powder components or is cured by kneading two components, paste and other paste. This material is disadvantageous in that the eugenol gives out a peculiar bad odor, and has a stimulating action on the hard and soft tissues of the oral cavity. Accordingly, when this material is used as an impression material for obtaining an impression of the hard and soft oral tissues, it sometimes comes in contact with the oral mucosa of a patient to causes severe pain to the patient and, in particular, causes intolerable pain to a patient whose mouth is inflamed or injured.

In addition, special care must be taken of allergic patients or dental surgeons since, even when they merely touch this material, it brings about an allergic reaction to them.

Furthermore, the supply of eugenol depends on the situation of affaires in the Western Africa, a main producer of eugeno. Hence, its price is precarious and high.

For these reasons, extensive investigations have been made for a long time on a novel material which is substantially free from any eugenol, but is still equivalent or superior thereto. For example, Japanese Patent Publication No. 24610/1961 describes that a composition which is similar in performance to a reaction product of zinc oxide and eugenol is obtained by saponifying an aliphatic carboxylic acid of the middle class with the use of a metal oxide to form an insoluble metallic soap. Since the saponification reaction proceeds slowly in this case, however, it is required to activate the reaction with the aid of a lower fatty acid and under the presence of a considerable amount of a resin acid such as rosin, leading to an excessive increase in the consistency of the resultant formulation. As a result, the formulation offers marked resistance to kneading. In addition, when a relatively lower fatty acid is used so as to raise the reactivity of the resultant composition, the composition is liable to emit an offensive odor peculiar to the lower fatty acid.

On the other hand, the use of a higher fatty acid was disadvantageous in that it does not only lower the reactivity of the composition, but also raises the melting point thereof when it is formulated in the form of paste, thus rendering it difficult to employ the same at lower temperatures.

SUMMARY OF THE INVENTION

The foundation of the present invention is to obtain a hard solid product by allowing reactive components consisting of oxides, hydroxides, basic salts and/or silicates of alkaline earth metals, aluminium and/or heavy metals to react with acid phosphates which are substantially free from any offensive odor, has a viscosity capable of being freely adjusted due to its low density and is of reactivity.

DETAILED DESCRIPTION OF THE INVENTION

According to the present invention, it is possible to use the acid phosphates alone or in the presence of liquid organic carboxylic acids and/or resin with a view to adjusting the viscosity and consistency of the final composition so as to improve the workability thereof.

The term "acid phosphates" used here generally refers to all the partial ester compounds of orthophosphoric acid formed by way of alcohols, and implies monoesters or diesters depending upon the number of substituents as shown in the following structural formulae:

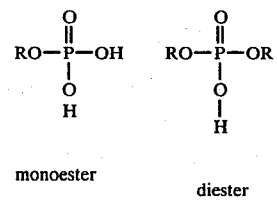

monoester    diester wherein R stands for alkyl groups. These free acid radicals can not only be submitted and additional reaction by polyalkylene oxides, but also be obtained in the form of their derivatives such as metallic salts, ammonium salts, amine salts etc. These derivatives have been employed as polymerization catalysts for synthetic resin, agents for extracting rare metals, rust preventives, additives for lubricant or the like.

It has now been found that a hard solid product which is set such that it can be used for dental purposes is obtained by allowing these acid phosphates which are liquid at room temperatures to mix and react with one of slightly soluble oxides, hydroxides, basic salts and silicates of di- or more-valent metals or a mixture thereof at a properly regulated reaction rate.

The acid phosphates which can be applied to the present invention are substantially water-insoluble liquid acids at room temperature, and monoalkyl acid phophates, dialkyl acid phophates, in which one or two of three hydrogens of orthophosphoric acid are replaced with one or two alkyl groups.

The present invention mainly employs the monoalky (dialkyl) acid phophates as liquid acids which are easily available.

Of the alkyl acid phosphates, various acid phosphates are obtained according to the number of the alkyl group(s), including mono-(or di-) propyl acid phosphate, mono-(or di-) butyl acid phosphate, mono-(or di-) octyl phosphate, mono-(or di-) isodecyl acid phosphate, mono-(or di) tridecanol acid phosphate and the like. It is possible to regulate the setting rate and the strength of a set product by using these phosphates alone or in combination therewith.

It is noted, however, that the less the number of carbon atoms the greater is the water solubility of the phophate with one substituent rather than that with two substituents, resulting in a steep rise in the reaction rate. On the contrary, the more the number of carbon atoms, the less the reaction rate. Hence, the critical number of carbon atoms is 13 in practice.

For this reason, the alkyl group(s) which can be applied to the present invention is limited to that having 3 to 13 carbon atoms. Paticular preference is given to the mono- or di-substituted phosphates or a proper combination thereof.

The metallic salt components allowed to react with the acid phosphates do not include any monovalent salts such as alkali metals and ammonium since the set product has to show insolubility with respect to water. As the effective reactants which are essentially insoluble in water, but are capable of reactng with acids, use can be made of di- or more-valent metallic salts such as oxides, hydroxides, basic salts, silicates etc. of aluminium and heavy metals, e.g., zinc, bismuth, lead, nickel, iron and copper, in addition to those of alkaline earth metals such as magnesium, calcium, barium, strontium and the like. For use, these salts may be powdered as minutely as possible, or may be mixed with an appropriate oily material to form paste. These reactive multivalent metallic salts may also be used in the form of a mixture thereof.

It has further be found that, in the reaction of the acid phosphates with such reactive multivalent metallic salts, small amounts of fluorine compounds, particularly sparing soluble fluorides, silicofluorides, titanium fluorides, zirconium fluorides and the like can advantageously be added as a third ingredient for promoting the setting rate without adversely affecting the properties of the set product. In other words, when the acid phosphates are permitted to react with the oxides, hydroxides, basic salts and silicates of multivalent metals which are sparing soluble in water, the reactivities of these metallic salts are determined by their affinities with respect to the residual acid group(s) of the acid phosphate, and it is then found that the acid dissolution of these sparing soluble salts proceeds more efficiently under the presence of small amounts of fluorine compounds.

As the easily available fluorine compounds which are hardly soluble in water, there are mentioned lithium fluoride, magnesium fluoride, calcium fluoride, barium fluoride, strontium fluoride, iron fluoride, zinc fluoride, manganese fluoride, nickel fluoride, copper fluoride, sodium silicofluoride, potassium silicofluoride, sodium titanium fluoride, potassium titanium fluoride, sodium zirconium fluoride, potassium zirconium fluoride etc.

The concentration of the fluorine compound is critically determined by the balance established between the equivalent of the effective acid radical and that of the metal base, and is such that it is uniformaly dispersed in the liquid acid, or causes the activity of the metal salt to suffer no lowering due to its internal reaction therewith. By preference, therefore, the concentration of the fluorine compound is restricted to less than 50% by weight of the acid phosphate. The lower limit thereof is determined by the activity of the metal salt, and is effectively 5% by weight of the acid phosphate.

Accordingly, the amount of the fluorine compound to be added is restricted to the range of 5 to 50% by weight of the acid phosphate. Furthermore, the acid components, i.e., acid phosphates, serving as the first components may be present together with mono- or more- valent organic carboxylic acid having 6 or more carbon atoms which are liquid at room temperature. This is because the organic carboxylic acid having 5 or less carbon atoms cannot provide a sufficient strength to the set product and is not practically suitable due to its stimulating action and peculiar offensive odor. Thus the use of the organic carboxylic acid having 6 or more carbon atoms along with the acid phosphates permits smooth progress of the reaction and, at the same time, makes it possible to use the latter in combination with the oxides, hydroxides, basic salts and silicates of metals which are less reactive only be the use of the organic carboxylic acids. The set product can also be endowed with the water resistance of a fatty acid soap.

In practice, the amounts of the acid phosphates to be used range from 0.5 to 60% by weight based on the total weight of the acid phosphates and the organic carboxylic acid. That is to say, the use of the acid phosphates in amounts of more than 0.5% by weight permits sufficient progress of the reaction of the organic carboxylic acids with the metallic salts difficult to react therewit. However, as the amounts of the acid phosphates are increased, the strength of the set product has a strong tendency to drop due to the concurrence of the reactions of the acid phosphates with the organic carboxylic acid and the metallic salts. Hence, when the acid phosphates are used in amounts of 1.5 times those of the organic carboxylic acids, i.e., more than 60% by weight of the total weight of the acid components, it is impossible to endow the set product with a strength enough to withstand practical use.

However, it is then possible to add as an auxiliary component for assisting setting one or more of liquid carboxylic acids having 5 or less carbon atoms such as movovalent carboxylic acids, for instance, acetic acid, levulinic acid, crotonic acid, acrylic acid or the like, and di- or more-valent solid carboxylic acids having a melting point of lower than 200° C., for instance, oxalic acid, malonic acid, succinic acid, glutaric acid, adipic acid, suberic acid, azelaic acid, sebacic acid, pentatricarboxylic acid, citric acid, hydroxyisobutyric acid or the like. This addition may be affected during the dissolution of the reactants by heating to improve the setting rate and state.

As the liquid carboxylic acids having 6 or more carbon atoms, use can be made of caproic, caprylic, capric, undecylic, pelargonic, erucic, octylic, oleic and linolenic acids. As special acids, use can be made of naphthenic, rosin, dimer, trimer acids and other acids.

These carboxylic acids are advantageously provided in the form of paste since they are easily mixed with other reactants during use. A specific resin is then added to the acid phophates or a mixture thereof with the organic carboxylic acid(s) for the purpose of endowing the paste with a viscous property. The resin does not only provide viscosity to the paste, but serves as an auxiliary agent for permitting smooth progress of the setting reaction. For this purpose, preference is given to rosin, a derivative thereof, maleic resin and modified maleic resin having an effective carboxyl group which partially participate in the reaction involved. It is also advantageous to employ a compatible resin free from any carboxyl group such as petroluem resin, ethyl cellulose, vinyl acetate, a copolymer of ethylene and vinyl acetate, ester rubber or the like. The rate of reaction between the acid phophates or a mixture thereof with the organic carboxylic acid(s) and the reactive multivalent metallic salts is dependent not only on ambient temperature and humidity but on the chemical properties of these reactants. When the reaction proceeds too rapidly, the cured product is obtained in the form of particles which are not suitable for the object of the present invention. The object of the present invention is to prepare a dental kneadable composition which is useful as a hard solid product having a setting time of more than one minute by properly adjusting the reaction to set the reaction product such that its molecules are entangled with each other as much as possible.

The rate of reaction may be regulated at need by the addition of a retarder such as an alcohol or an accelerator such as a solid multivalent carboxylic acid or a liquid organic carboxylic acid having 5 or less carbon atoms.

The aforesaid fundamental components may be added with other components for various purposes or so as to especially attain the required properties. That is to say, a known material may be added so as to eliminate the smell and taste of these components, or small amounts of white carbon, viscous agents, sterilizers, chemicals and the like may be added for secondary improvement purposes.

The amount of the fluorine compound serving as a reaction-assisting agent is determined in connection with the amount of the acid phosphates, and is preferably in the range of 50 to 5% by weight of the acid phosphates.

The fundamental composition of the present invention will now be summarized.

1. At least one of acid phosphates obtained by replacing one or two hydrogen atoms of orthophosphoric acid with alcohols having 3 to 13 carbon atoms.
2. At least one of liquid organic carboxylic acids having 6 or more carbon atoms, which can be mixed with at least one of acid phosphates obtained by replacing one or two hydrogen atoms or orthophosphoric acid with alcohols having 3 to 13 carbon atoms.
3. At least one of reactive multivalent metallic salts which can react with the acid phosphates formed by replacing one or two hydrogen atoms of orthophosphoric acid with alcohols having 3 to 13 carbon atoms or a mixture thereof with liquid organic carboxylic acids having 6 or more carbon atoms.
4. Fluorine compound (fluoride, silicofluoride, titanium fluoride, zirconium fluoride) which serve as a reaction-assisting agent.
5. Liquid organic carboxylic acid having 5 or less carbon atoms which serves as a reaction accelerator.
6. Di- or more- valent solid organic carboxylic acid having a melting point of less than 200° C. which serve as a reaction regulator.
7. Resinous material having an effective carboxyl group which are added as a material for permitting smooth progress and support of the reaction in amount of less than 80% by weight of the total composition.

The aforesaid fundamental components are properly selected and allowed to react with each other to endow the resultant reaction product to be set with the properties useful as a dental material. The amounts of the acid phosphate(s) and/or the liquid organic carboxylic acid(s) are in the range of 8 to 92% by weight, and the total amounts of the reactive multivalent metallic salts are correspondingly in the range of 92 to 8% by weight.

When the acid components comprise a combination of the acid phosphates and the liquid organic carboxylic acids, they are sometimes permitted to react with the reactive multivalent metallic salts at a given rate but in an insufficient settng time. The reaction may then be accelerated with the aid of the lower organic carboxylic acid having 5 or less carbon atoms in amounts of less than 10% by weight of the acid components, or be retarded with the use of the solid multivalent organic carboxylic acid having a melting point of lower than 200° C. Alternatively, the setting time may freely be regulated by the use of both carboxylic acids in different amounts.

Thus, the acid components may be the acid phosphates alone or a mixture thereof with the liquid organic carboxylic acids. In either case, the setting reaction time may be regulated by varying the amount of the fluorine compound to be added.

It is noted that the resin material having an effective carboxyl group which is added in amounts of less than 80% by weight of the total composition does not only provide viscosity to the liquid reaction product, but also results in acceleration of the setting raction as well as an increase of the hardness of the set solid product. As the resin which can be used together with the acid phosphates and is compatible with respect thereto, there are mentioned rosin, modified rosin, maleic resin, modified maleic resin, a copolymer resin of ethylene and vinyl acetate, ethyl cellulose, petroleum resin and the like.

The dental composition of the present invention finds use in various dental therapeutic applications including filling, temporary filling, fixing and impression.

The present invention will now be described in detail with reference to examples, but is not limited thereto.

EXAMPLE 1

Dioctyl acid phosphate: 56% by weight
Basic aluminium sulfate: 44% by weight

The liquid dioctyl acid phosphate was sufficiently mixed with the powdery basic aluminium sulfate, and was allowed to stand at room temperature. After the lapse of about 2 minutes, the resultant product was cured to obtain a hard solid product having a compression strength of 44 Kg/cm$^2$ determined after one hour. This solid product was found to be excellent since the acid phosphate reacted keenly with respect to the basic aluminium sulfate.

After immersed in water of 37° C. for one month, the obtained solid product underwent neither softening nor deterioration. Thus, this product is an extremely stable material in comparison with the known zinc oxide/eugenol based material, and can be utilized as a dental material.

When the amount of the basic aluminium sulfate was decreased, the setting time was extended. Hence, the setting time could be adjusted by varying the ratio of both components, but it was found that some limitations has to be placed on the ratio since the consistency of the mixture undergoes a change during kneading

EXAMPLE 2

Monobutyl acid phosphate: 12% by weight
Dioctyl acid phosphate: 18% by weight
Diisodecyl acid phosphate: 33% by weight
Basic aluminium acetate: 27 by weight
Magnesium silicate: 10% by weight The aforesaid three acid phosphates were mixed together to form an uniform solution which was, in turn, kneaded and mixed with an uniform mixture of the two powdery components. The resultant product was cured in about 30 minutes at room temperature to obtain a solid product having a compression strength of 55 Kg/cm$^2$ determined after one hour. It was found that the smaller the molecular weight of the acid phosphates used (the number of carbon atoms in the alkyl group(s)), the faster the progress of the setting reaction, but the set product is brittle. It was furthermore found that the strength of the set product increases with an increase in the molecular weight, i.e., an increase in the number of carbon atoms in the alkyl group(s). Thus, it was possible to regulate the setting time and the strength of the set product by the proper combination of low- and high-molecular weight acid phosphates and the selection of the amounts and kinds of the reactants.

EXAMPLE 3

Monooctyl acid phosphate: 21% by weight
Dibutyl acid phosphate: 40% by weight
Zinc oxide: 30% by weight
Magnesium silicate: 3% by weight
Sodium titanium fluoride: 6% by weight The aforesaid two acid phosphates were uniformly mixed together to form a liquid component which was, in turn, kneaded and mixed with a powdery component obtained by uniformly mixing together the zinc oxide, magnesium silicate and sodium titanium fluoride. The resultant product was allowed to stand at room temperature. The product was then cured in about 8 minutes to obtain a solid product having a compression strength of 40 Kg/cm$^2$ determined after one hour. It was found that the addition of the oxide, hydroxide and basic salt of metals especially together with a sparing soluble fluorine compound in the form of a fluoride, silicofluoride, titanium fluoride or zirconium fluoride permits activation of the setting reaction and easy progress thereof.

EXAMPLE 4

Dioctyl acid phosphate: 10% by weight
Undecylic acid: 31% by weight
Zinc hydroxide: 57% by weight
Magnesium hydroxide: 2% by weight The acid phosphate and undecylic acid were uniformly mixed together to form a liquid component which was then kneaded and mixed with a powdery component prepared by homogeneously mixing the zinc hydroxide and magnesium hydroxide. The resultant product was allowed to stand at room temperature. The product was then cured in about 12 minutes to obtain a solid product having a compression strength of 33 Kg/cm$^2$ determined one hour after setting.

EXAMPLE 5

Component A
  Dibutyl acid phosphate: 51% by weight
  Dioctyl acid phosphate: 15% by weight
  Caprylic acid: 26% by weight
  Ethyl cellulose: 8% by weight
Component B
  Zinc oxide: 56% by weight
  Aluminium hydroxide: 36% by weight
  Potassium fluoride: 8% by weight The component A was prepared in the form of an uniform paste by adding the caprylic acid and ethyl cellulose to a liquid obtained by mixing together the two acid phosphates, and by heating under agitation the resultant product at 100° C. Next, the component B was prepared in the form of powder by uniformly mixing together the zinc oxide, aluminium hydroxide and potassium flouride. The components A and B were kneaded together in a weight ratio of ½ and were sufficiently mixed. The resultant product was allowed to stand at room temperature. The preduct was then cured in about 5 minutes to obtain a hard solid product having a compression strength of 58 Kg/cm$^2$ determined after one hour. It was found that it is possible to provide viscosity to the liquid component by dissolving in the acid phosphate the resin soluble therein such as ethyl cellulose or a copolymer of ethylene/vinyl acetate, or by suspending therein the inorganic filler such as colloidal silica, thus making easy the kneading and mixing operations.

EXAMPLE 6

Component A
  Isodecyl acid phosphate: 12% by weight
  Octylic acid: 7% by weight
  Capric acid: 76% by weight
  Levulinic acid: 5% by weight
Component B
  Zinc oxide: 78% by weight
  Magnesium oxide: 2% by weight
  Olive oil: 16% by weight
  Liquid paraffin: 4% by weight The component A was prepared in the form of an uniform liquid by mixing under sufficient agitation the acid phosphate (isodecyl acid phosphate) with the octylic, capric and levulinic acids at room temperature. Next, the component B was prepared in the form of an uniform paste by mixing together the zinc oxide and magnesium oxide powders, and sufficiently mixing the thus obtained mixture with the olive oil and liquid paraffin by means of a grinding machine. The components A and B were kneaded in a weight ratio of ⅓ and were sufficiently mixed together. The resultant mixture was allowed to stand at room temperature. The mixture was then cured in about 10 minutes to obtain a hard solid product having a compression strength of 42 Kg/cm$^2$ determined after one hour.

It was found that the lower liquid organic carboxylic acids having 5 or less carbon atoms such as levulinic acid, acetic acid and the like can be used in amounts of several percents of the total acid components since they permit marked acceleration of the setting reaction. When the entire reaction proceeds more slowly, such lower carboxylic acids could be used in greater amounts. At amounts exceedng 10% by weight, however, the balance between the lower liquid organic carboxylic acids and the fundamental components was destroyed so that only the carboxylic acids underwent a local reaction to bring about the reaction product in the form of granule. In addition, the obtained product considerably gave out offensive and stimulating smells peculiar to such lower carboxylic acids. For these reasons, the amounts of the lower liquid organic carboxylic acids used were limited to less than 10% by weight of the total acid components.

EXAMPLE 7

Component A
  Dioctyl acid phosphate: 9% by weight
  Pelargonic acid: 58% by weight
  Trimer acid: 28% by weight
  Glutaric acid: 5% by weight
Component B
  Zinc oxide: 70% by weight
  Zinc hydroxide: 8% by weight
  Liquid paraffin: 18% by weight
  Lanolin: 4% by weight The component A was prepared in the form of an uniform liquid by heating under agitation the three acids, pelargonic, trimer and glutaric acids at 100° C. to obtain an uniform liquid, and cooling the obtained liquid to about 70° C. and adding thereto the dioctyl acid phosphate followed by mixing. Next, the component B was prepared in the form of a homogeneous paste by mixing together the zinc oxide and zinc hydroxide powders and adding to the resultant mixture the liquid paraffin and lanolin followed by sufficient mixing by means of a grinding machine. The components A and B were kneaded in a weight ratio of ½, and the resultant mixture was allowed to stand at room temperature. The mixture was then cured in about 7 minutes to obtain a hard solid product having a compression strength of 50 kg/cm² determined one hour after setting.

It was found that the di- or more- valent solid carboxylic acids having a melting point of less than 200° C. such as glutraric acid, succinic acid and the like show good compatibility with respect to the acid phosphates and the liquid organic carboxylic acids having 6 or more carbon atoms in amounts of less than 10% by weight of the total acid components, and permit acceleration of the setting reaction with the reactive multivalent metallic salts like the liquid organic carboxylic acids having 5 or less carbon atoms. It was furthermore found that the solid carboxylic acids have a thixotropic action on a pasty kneaded product in kneading, so that the pasty product is prevented from falling in drops. At amounts exceeding 10% by weight, however, the solid acids were foutd to be easily separated fom the pasty product cooled down to room temperature, resulting in a lowering of the workability. Thus the concentration of the solid acids was limited to 10% by weight of the total acid contents.

EXAMPLE 8

Component A
 Dioctyl acid phoshate: 26% by weight
 Perlargonic acid: 38% by weight
 Ester gum: 36% by weight
Component B
 Zinc oxide: 49% by weight
 Bismuth hydroxide: 12% by weight
 Magnesium oxide: 6% by weight
 Sodium fluoride 6% by weight
 Peanut oil: 27% by weight The component A was prepared in the form of an uniform paste by heating under agitation the pelargonic acid and ester gum at 130° C. to permit dissolution thereof, cooling down the resultant product to about 50° C. and adding thereto the dioctyl acid phosphate followed by sufficient mixing. Next, the component B was prepared in the form of an uniform paste by sufficiently mixing together the abovementioned four powdery components such as zinc oxide and adding to the resultant product the peanut oil followed by ample mixing by means of a grinding machine. The components A and B were kneaded in a weight ratio of ½, and the obtained product was allowed to stand at room temperature. The product was then cured in about 7 minutes to obtain a hard solid product having a compression strength of 52 Kg/cm² determined one hour after setting.

It was also possible to select the setting time by varying the weight ratio of the component A to B.

EXAMPLE 9

Component A
 Dioctyl acid phosphate: 13% by weight
 Dimer acid 48% by weight
 Rosin-modified maleic resin 34% by weight
 Acrylic acid 3% by weight
 Succinic acid 2% by weight
Component B
 Zinc oxide: 55% by weight
 Calcium silicate: 5% by weight
 Nickel hydroxide: 7% by weight
 Potassium zirconium fluoride 4% by weight
 Camellia oil 29% by weight The rosin-modified maleic resin was esterified by glycerol, but has still an effective carboxyl group.

The component A was prepared in the form of an uniform paste by heating under agitation the dimer acid, succinic acid and rosin-modified maleic acid at 130° C. to allow uniform dissolution thereof, cooling the resultant product to about 50° C. and adding thereto the dioctyl acid phosphate and acrylic acid followed by sufficient mixing. Next, the component B was prepared in the form of an uniform paste by sufficiently mixing together the aforesaid four powdery components such as zinc oxide and adding the camellia oil to the resulting mixture followed by ample mixing by means of a grinding machine.

The components A and B were kneaded in a weight ratio of ½, and the resultant product was allowed to stand at room temperature. The product was then cured in about 8 minutes to obtain a hard solid product having a compression strength of 85 Kg/cm² determined one hour after setting.

The incorporation of the resin having an effective carboxyl group was found to be effective for the provision of a strength to the solid product.

While the invention has been described in detail and with reference to specific examples thereof, it will be apparent to one skilled in the art that various changes and modifications can be made therein without departing from the spirit and scope thereof.

What is claimed is:

1. A dental composition comprising a combination of 8 to 92% by weight of liquid acid phosphates obtained by replacing one or two hydrogen atoms of orthophosphoric acid with alcohols having 3 to 13 carbon atoms and being essentially insoluble in water, 92 to 8% by weight of at least one of reactive multivalent metallic salts selected from the group consisting of oxides, hydroxides, basic salts and silicates of alkaline earth metals, aluminium of heavy metals, and 50 to 5% by weight of at least one of sparing soluble fluorides, silicofluorides, titanium fluorides and zirconium fluorides serving as a reaction accelerator based on the weight of said acid phosphates, said compounds being permitted to react with each other such that they are cured at room temperature.

2. A dental composition according to claim 1, including further at least one of resins having an effective carboxyl group in amounts of less than 80% by weight of the total components.

3. A dental composition composing a combination of 8 to 92% by weight of acid components consisting of 0.5 to 60% by weight of liquid acid phosphates obtained by replacing one or two hydrogen atoms of orthophosphoric acid with alcohols having 3 to 13 carbon atoms and being essentially insoluble in water and the remainder being at least one of mono- or more- valent liquid organic carboxylic acids having 6 or more carbon atoms and being liquid at room temperature, 92 to 8% by weight of at least one of reactive multivalent metallic salts selected from the group consisting of oxides, hydroxides, basic salts and silicates of alkaline earth metals, aluminium and heavy metals, and at least one of sparing soluble fluorides, silicofluorides, titanium fluorides and zirconium fluorides which serve as a reaction accelerator and are added in amounts of less than 50 to 50% by weight of said acid phosphates, said compounds being permitted to react with each other such that they are cured at room temperature.

4. A dental composition according to claim 3, including further at least one of resins having an effective carboxyl group in amounts of less than 80% by weight of the total components.

5. A dental composition comprising a combination of 8 to 92% by weight of acid components consisting of 0.5 to 60% by weight of liquid acid phosphates obtained by replacing one or two hydrogen atoms of orthophosphoric acid with alcohols having 3 to 13 carbon atoms and being essentially insoluble in water and the remainder being at least one of mono- or more- valent liquid organic carboxylic acids having 6 or more carbon atoms and being liquid at room temperature, 92 to 8% by weight of at least one of reactive multivalent metallic salts selected from the group consisting of oxides, hydroxides, basic salts and silicates of alkaline earth metals, aluminium and heavy metals, at least one of di- or more- valent solid organic carboxylic acids having a melting point of lower than 200° C. or liquid organic carboxylic acids having 5 or less carbon atoms which are added in amounts of less than 10% by weight of said acid components, and at least one of sparing soluble fluorides, silicofluorides, titanium fluorides and ziroconium fluorides which are added as a reaction accelerator in amounts of 50 to 5% by weight based on the quantities of said acid phosphates, said compounds being permitted to react with each other such that they are cured at room temperature.

6. A dental composition according to claim 5, including further at least one of resins having and effective carboxyl group in amounts of less than 80% by weight of the total components.

* * * * *